US006692965B1

(12) United States Patent
Shekdar et al.

(10) Patent No.: US 6,692,965 B1
(45) Date of Patent: Feb. 17, 2004

(54) ISOLATION OF LIVING CELLS AND PREPARATION OF CELL LINES BASED ON DETECTION AND QUANTIFICATION OF PRESELECTED CELLULAR RIBONUCLEIC ACID SEQUENCES

(75) Inventors: Kambiz Shekdar, New York, NY (US); Gunter Blobel, New York, NY (US)

(73) Assignee: Chromocell Corporation, North Brunswick, NJ (US)

( * ) Notice: Subject to any disclaimer, the term of this patent is extended or adjusted under 35 U.S.C. 154(b) by 0 days.

(21) Appl. No.: 09/718,448

(22) Filed: Nov. 22, 2000

Related U.S. Application Data

(60) Provisional application No. 60/166,987, filed on Nov. 23, 1999.

(51) Int. Cl.[7] .......................... C12N 15/85; C12N 15/63; C07H 21/04
(52) U.S. Cl. ..................... 435/455; 536/23.1; 536/23.2; 536/23.4; 536/23.5; 536/24.1; 536/24.2; 536/24.3; 536/24.31; 536/24.32; 424/93.21; 424/93.7; 435/320.1; 435/471
(58) Field of Search .............................. 536/23.1, 23.2, 536/23.4, 23.5, 24.1, 24.2, 24.3, 24.31, 24.32; 424/93.21, 93.7; 435/320.1, 455.471

(56) References Cited

U.S. PATENT DOCUMENTS

| 5,641,675 A | 6/1997 | Singer et al. ................ 435/325 |
| 5,925,517 A | 7/1999 | Tyagi et al. .................... 435/6 |
| 6,203,986 B1 | 3/2001 | Singer et al. ................... 435/6 |
| 2002/0090614 A1 | 7/2002 | Zhang et al. ................... 435/6 |

FOREIGN PATENT DOCUMENTS

| WO | WO 91/07660 | * 5/1991 |

OTHER PUBLICATIONS

Sokol et al., Real time detection of DNA–RNA hybridization in living cells, 1998, Proc. Natl. Acad. Sci. USA, vol. 95, pp. 11538–11543.*
Gagneten et al., Brief expression of GFP cre fusion gene in embryonic stem cells allows rapid retrieval of site-specific genomic deletions, 1997, Nucleic Acids Research, vol. 25, pp. 3326–3331.*
S.Kitazawa et al., "In Situ DNA–RNA Hybridization Using in Vivo Bromodeoxyuridine–Labeled DNA Probe," *Histochemistry,* vol. 92, pp. 195–199 (1989).

Q.–G. Li et al., "Molecular Beacon–Based Homogeneous Fluorescence PCR Assay for the Diagnosis of Infectious Diseases," *Analytical Sciences,* vol. 16, pp. 245–248 (2000).
G. Leone et al., "Molecular Beacon Probes Combined with Amplification by NASBA Enable Homogeneous, Real–Time Detection of RNA," *Nucleic Acids Research,* vol. 26, No. 9, pp. 2150–2155 (1998).
M.E. Martone et al., "Subcellular Localization of mRNA in Neuronal Cells," *Molecular Neurobiology,* vol. 18, pp. 227–246 (1998).
T. Matsuo, "In Situ Visualization of Messenger RNA for Basic Fibroblast Growth Factor in Living Cells," *Biochimica et Biophysica Acta,* 1379, pp. 178–184 (1998).
K.J. Pennline et al., "Detection of In Vivo–Induced IL–1 mRNA in Murine Cells by Flow Cytometry (FC) and Fluorescent In Situ Hybridization (FISH)," *Lymphokine and Cytokine Research,* vol. 2, No. 1, pp. 65–71 (1992).
J. Phillips et al., "Antisense RNA Amplification: A Linear Amplification Method for Analyzing the mRNA Population from Single Living Cells," *Methods: A Companion to Methods in Enzymology,* vol. 10, No. 3, pp. 283–288 (1996).
S. Sixou et al., "Intracellular Oligonucleotide Hybridization Detected by Fluorescence Resonance Energy Transfer (FRET)", *Nucleic Acids Research,* vol. 22, No. 4, pp. 662–668 (1994).
A. Tsuji et al., "Direct Observation of Specific Messenger RNA in a Single Living Cell under a Fluorescence Microscope," *Biophysical Journal,* vol. 78, pp. 3260–3274 (Jun. 2000).
S. Tyagi et al., "Multicolor Molecular Beacons for Allele Discrimination," *Nature Biotechnology,* vol. 16, pp. 49–53 (1998).
S. Tyagi et al., "Molecular Beacons: Probes that Fluoresce Upon Hybridization," *Nature Biotechnology,* vol. 14, pp. 303–308 (1996).

* cited by examiner

*Primary Examiner*—James Ketter
*Assistant Examiner*—Daniel M Sullivan
(74) *Attorney, Agent, or Firm*—Fish & Neave; Jane T. Gunnison; Li Su

(57) ABSTRACT

The invention is directed to reliable and efficient detection of mRNAs as well as other RNAs in living cells and its use to identify and, if desired, separate cells based on their desired characteristics. Such methods greatly simplify and reduce the time necessary to carry out previously-known procedures, and offers new approaches as well, such as selecting cells that generate a particular protein or antisense oligonucleotide, generating cell lines that express multiple proteins, generating cell lines with knock-out of one or more protein, and others.

33 Claims, No Drawings

ISOLATION OF LIVING CELLS AND PREPARATION OF CELL LINES BASED ON DETECTION AND QUANTIFICATION OF PRESELECTED CELLULAR RIBONUCLEIC ACID SEQUENCES

CROSS-REFERENCE TO RELATED APPLICATION

This application claims priority to provisional application serial No. 60/166,987, filed Nov. 23, 1999, incorporated herein by reference in its entirety.

BACKGROUND OF THE INVENTION

A molecular beacon is a nucleic acid probe that recognizes and reports the presence of a specific nucleic acid sequence. The probes are hairpin-shaped sequences with a central stretch of nucleotides complementary to the target sequence, and termini comprising short mutually complementary sequences. One terminus is covalently bound to a fluorophore and the other to a quenching moiety. When in their native state with hybridized termini, the proximity of the fluorophore and the quencher is such that no fluorescence is produced. The beacon undergoes a spontaneous fluorogenic conformational change when hybridized to its target nucleic acid. See, for example, U.S. Pat. No. 5,925,517.

This property has enabled researchers to detect specific nucleic acids primarily in in vitro reactions and in some cases even in living cells. In-situ visualization of messenger RNA has been achieved using molecular beacons delivered to living-cells in liposomes (Matsuo, 1998, Biochim. Biophys. Acta 1379:178–184). Studies involving cells have to date employed beacons generated with the very weak fluorophore EDANS as this was the only one known to be quenched by the quencher EDAC. The results though discernible are barely so and the applicability of this line of research to in-vivo detection was not promising.

SUMMARY OF THE INVENTION

In one aspect, the present invention is directed to a method for generating a cell line expressing at least one preselected protein comprising the steps of:
  a) transfecting a cell line with at least one DNA construct encoding at least one preselected protein and at least one drug resistance marker;
  b) selecting for cells resistant to a drug to which said marker confers resistance, said cells transcribing the at least one drug resistance marker;
  c) exposing the selected cells to a first molecular beacon that fluoresces upon hybridization to an RNA transcript of the at least one preselected protein;
  d) isolating the cells that fluoresces;
  e) generating a cell line expressing the at least one preselected protein by growing the isolated cells.

The aforementioned method may be carried out using fluorescence activated cell sorter technology. In a further aspect, the cell line may be made to express a second preselected protein by carrying out further steps including transfecting the cell line with a second DNA construct encoding a second preselected protein and a second drug resistance marker; selecting for cells expressing the second marker; exposing the cells to a second molecular beacon which fluoresces upon hybridization to an RNA transcript of the second preselected protein and isolating cells that exhibit fluorescence of each of the at least one and the second mRNA transcripts. Cell lines expressing more than two proteins may be provided by repeating the steps. The method to introduce the second protein may be performed either simultaneously or sequentially. If the first and second drug resistance markers are the same, simultaneous selection may be achieved by increasing the level of the drug.

In another aspect of the invention, a method is provided for generating a cell line expressing at least one preselected protein comprising the steps of:
  a) transfecting a cell line with at least one DNA construct encoding the at least one preselected protein, at least one drug resistance marker and at least one first epitope tag;
  b) selecting for cells resistant to a drug to which said marker confers resistance, said cells transcribing the at least one drug resistance marker;
  c) exposing the cells to a first molecular beacon that fluoresces upon hybridization with the RNA transcript of the first epitope tag;
  d) isolating the cells that fluoresce; and
  e) generating a cell line expressing the at least one preselected protein by growing the isolated cells.

The aforementioned method may be carried out using a fluorescence activated cell sorter technology. The DNA portion of the construct encoding the epitope tag may be in frame or out of frame with the portion of the DNA construct encoding the at least one protein. In a further embodiment, the cell line may be made to express at least a second preselected protein; the steps further including transfecting the cell line with a second DNA construct encoding the second preselected protein, a second drug resistance marker and a second epitope tag, selecting for cells transcribing the second marker; exposing the cells to a second molecular beacon that fluoresces upon hybridization with the RNA transcript of the second epitope tag, and isolating the cells that exhibit fluorescence of each of the first and the second epitope tag. In the case of two proteins, the portion of the DNA sequence encoding the second epitope tag may also be in frame or out of frame with the portion of the DNA sequence encoding the second protein. The second preselected protein may be transfected either simultaneously or sequentially with the first. Should the method be performed simultaneously, and the same drug resistance marker used for both constructs, a higher level of drug may be used to select for cells expressing both constructs. Furthermore, more than two proteins may be provided in the cell line by repeating the aforementioned steps.

In yet a further aspect of the present invention, a method is provided for generating a cell line expressing at least one preselected antisense RNA molecule comprising the steps of:
  a) transfecting a cell line with a DNA construct encoding the at least one preselected antisense RNA molecule and at least one drug resistance gene;
  b) selecting for cells resistant to a drug to which said marker confers resistance, said cells transcribing the at least one drug resistance marker;
  c) exposing the cells to a molecular beacon that fluoresces upon hybridization to the antisense RNA molecule;
  d) isolating the cells that fluoresce; and
  e) generating a cell line expressing the preselected antisense RNA sequence by growing the isolated cells.

Isolating the cells that fluoresce may be carried out using fluorescence activated cell sorter technology. The cell line may be made to express at least one second preselected antisense RNA molecule, the steps further including simultaneously or sequentially transfecting the cell line with a second DNA construct encoding a second preselected antisense RNA molecule and a second drug resistence marker; selecting for cellular expressing the second marker; exposing the cells to a second molecular beacon which fluoresces upon hybridization to a the second antisense RNA molecule; and isolating cells that exhibit fluorescence of each of the at least one and the second mRNA transcripts. If the method is performed simultaneously and the same drug resistance marker is used in both constructs, selection can be achieved using a higher level of drug. More than two antisense RNA molecules may be provided by repeating the aforementioned steps with another construct.

In yet another aspect of the invention, a method is provided for generating a cell line expressing at least one preselected antisense RNA molecule comprising the steps of:

a) transfecting a cell line with a DNA construct encoding the at least one preselected antisense RNA molecule, at least one drug resistance marker and a first epitope tag nucleotide sequence;

b) selecting for cells resistant to a drug to which said marker confers resistance, said cells transcribing the at least one drug resistance marker;

c) exposing the selected cells to a first molecular beacon that fluoresces upon hybridization to a mRNA transcript of the first epitope tag;

d) isolating the cells that fluoresce; and e) generating a cell line expressing the at least one preselected antisense RNA molecule by growing the isolated cells.

The cell line may be made to express at least one second preselected epitope tagged antisense RNA, the steps further including transfecting the cell line with a second DNA construct encoding a second preselected epitope-tagged antisense RNA molecule a second drug resistance marker; selecting for cellular expressing the second marker; exposing the cells to a second molecular beacon which fluoresces upon hybridization to an RNA transcript of the second epitope tag; and isolating cells that exhibit fluorescence of both the at least one and the second mRNA transcripts. These steps may be carried out simultaneously or sequentially with the first. Selection using simultaneous transfection with both constructs having the same drug resistance marker may be achieved by using a higher level of drug. Additional steps may be carried out to introduce more than two epitope-tagged antisense molecules.

The foregoing methods may be used to prepare cells expressing antisense RNA molecules or any other type of RNA molecule, including but not limited to structural RNAs, including rRNA, as well as hnRNA and snRNA. Furthermore, it should be noted that all of the methods in which an epitope tag is provided for detection by a molecular beacon of the transfected construct, it is unimportant whether the epitope tag is in frame or out of frame with the encoded protein, as long as the epitope tag sequence is detectable by the molecular beacon.

In yet a further aspect of the invention, a method is provided for isolating cells expressing at least one protein or RNA comprising the steps of:

a) providing cells suspected of expressing the at least one protein;

b) exposing the cells to at least one molecular beacon that fluoresces upon hybridization with a mRNA transcript encoding the at least one protein;

c) isolating the cells that fluoresce.

Fluorescence-activated cell sorter technology may be used to isolate the cells that fluoresce. The protein may be, by way of non-limiting example, a cell surface-localized protein or an intracellular protein. Any other RNA may also be detected. The method may also be used to identify cells also expressing a second protein or RNA, using a second molecular beacon which fluoresces upon hybridization with its target RNA is exposed to the cells, cells having fluorescence of each of the first and second molecular beacons are isolated. Simultaneous expression of more than two proteins is also achievable.

The present invention is also directed to a method for quantifying the level of at least one RNA transcript expression in a biological sample comprising the steps of:

a) exposing the biological sample to a first molecular beacon which fluoresces upon hybridization with the RNA transcript;

b) quantitating the level of fluorescence in the biological sample; and c) correlating the level of fluorescence with the level of the at least one RNA transcript.

The biological sample may be cellular sample or a tissue sample. The sample may be fixed. The RNA transcript may be, but is not limited to, RNA that encodes a protein, a structural RNA, or an antisense RNA. The fluorescence may be quantitated by fluorescence microscopy or fluorescence-activated cell sorter technology. The level of at least one second RNA transcript expression may also be quantified in the biological sample using a second molecular beacon which fluoresces upon hybridization to the second RNA transcript.

In still a further aspect of the invention, a method is provided for generating a cell line which overexpresses at least one protein comprising the steps of:

a) transfecting cells with at least two DNA sequences, one sequence having a portion encoding the protein, at least one epitope tag, and at least one drug resistance marker; and a second sequence having a portion encoding the protein, at least one second epitope tag, and at least one second drug resistance marker;

b) selecting for cells transfected with the at least two DNA sequences by expression of the first and the second drug resistance markers;

c) exposing the selected cells to a first and a second molecular beacon, each which fluoresces upon hybridization to the nucleotide sequences of RNA transcripts of the first and the second epitope tags respectively;

d) isolating the cells that exhibit fluorescence of each of the first and second molecular beacons; and e) generating a cell line overexpressing the at least one preselected protein by growing the isolated cells.

In the foregoing aspect of the invention, the at least two DNA sequences may reside on the same construct. The first and the second epitope tags may each independently be in frame or out of frame with the protein. The FACS may be used to isolate cells expressing both constructs by isolating the cells expressing the strongest fluorescence. As with the previous methods described herein, the transfection may be done simultaneously or sequentially. Selection when the same drug resistance marker is present in both constructs and simultaneous transfection is performed may be achieved by increasing the level of the drug.

In a further aspect, a method is provided for generating a cell line which overexpresses at least one antisense RNA molecule comprising the steps of:

a) transfecting cells with at least two DNA sequences, one sequence having a portion encoding the protein, at least one epitope tag, and at least one drug resistance marker; and a second sequence having a portion encoding the protein, at least one second epitope tag, and at least one second drug resistance marker;

b) selecting for cells transfected with the at least two DNA sequences by expression of the first and the second drug resistance markers;

c) exposing the selected cells to a first and a second molecular beacon, each which fluoresces upon hybridization to the nucleotide sequences of RNA transcripts of the first and the second epitope tags respectively;

d) isolating the cells that exhibit fluorescence of each of the first and second molecular beacons; and e) generating a cell line overexpressing the at least one preselected antisense RNA molecule by growing the isolated cells.

The at least two DNA sequences may reside on the same construct. The first and the second epitope tags may each independently be in frame or out of frame with the antisense RNA molecule. Conditions and alternative methods for achieving the desired product are as noted above. Furthermore, any form of RNA may be provided.

In another aspect of the invention, a method for generating cells functionally null for expression of at least one preselected protein or RNA is provided comprising the steps of providing in the cells a plurality of antisense RNAs to the preselected protein or RNA, wherein the plurality of antisense RNA to the at least one preselected protein or RNA binds essentially all RNA transcripts of the mRNA or other RNA to be eliminated. In the case of making cells null for a preselected protein, the preselected protein may be specifically only one or a subset of alternatively spliced forms of a gene product.

In a further aspect of the invention, a method is provided for generating a transgenic animal that is a functionally null-expressing mutant of at least one preselected protein comprising carrying out the steps as herein before described utilizing embryonic stem cells, determining the viability of the stem cells functionally null expressing the preselected protein, and using the viable embryonic stem cells to produce the transgenic animal.

Furthermore, a method for generating a cell line which is functionally null expressing at least one protein and overexpressing at least one other protein comprising carrying out the methods described herein on the same cells. In addition, a method for generating a cell line expressing a lethal antisense RNA under control of an inducible promoter is provided by carrying out the foregoing methods wherein step (a) is performed in the presence of a minimal amount of an inducer.

A method for identifying genetic recombinational events in living cells comprising the steps of:

a) exposing a cell to a molecular beacon that fluoresces upon hybridization with a RNA sequence selected from the group consisting of that transcribed from a recombined sequence and that transcribed from the nonrecombined sequence;

b) detecting or sorting said cells.

The detecting and/or sorting of the cells may be performed by FACS or microscope.

In another aspect, the present invention is directed to a proteolytic activity-generating unitary hybridization probe, herein referred to as a probe protease. Such probe proteases operate in a similar fashion to a molecular beacon, but instead of a change in fluorescence on interaction of the beacon with its target nucleic acid sequence, the probe protease becomes proteolytic in the presence of the target. The probe protease composition provides at one end of a molecular beacon-type oligonucleotide a protease, and at the other, a complementary protease inhibitor. When the oligonucleotide is not hybridized to a target sequence, the proximity of the ends of the oligonucleotide permit the protease and the protease inhibitor to interact, inhibiting proteolytic activity of the protease. However, upon hybridization of the target sequence of the oligonucleotide to the target, the protease and its inhibitor are separated, activating the protease. The activity of the protease can be readily measured, and furthermore, the active protease in the presence of a particular nucleic acid target sequence may be employed not only for detection purposes but also for therapeutic purposes, in which, for example, a cell in which the probe protease is delivered is proteolyzed and rendered nonviable if a particular gene is transcribed, for example, one related to cellular transformation, oncogenesis, dysproliferation, and the like.

The aforementioned probe may have a proteolytic enzyme inhibitor which is a peptide or another molecule capable of reversibly inactivating the enzyme. Non-limiting examples of enzymes and inhibitors include aminopeptidase and amastatin, trypsin-like cysteine proteases and antipain, aminopeptidase and bestatin, chymotrypsin like cysteine proteases and chymostatin, aminopeptidase and diprotin A or B, carboxypeptidase A and EDTA, elastase-like serine proteases and elastinal, and thermolysin or aminopeptidase M and 1,10-phenanthroline.

These and other aspects of the invention will be appreciated from the following detailed description.

DETAILED DESCRIPTION OF THE INVENTION

The invention herein is based upon the ability of molecular probes to identify RNA sequences in living cells, and the use of fluorescence cell sorter or related technology to identify and/or separate cells exhibiting a certain level or levels of fluorescence at one or more wavelengths. It is now known that EDAC can quench the emissions of a variety of the strongest commonly-used fluorophores. Being able to detect reliably and efficiently mRNAs as well as other RNAs in living cells enables their use to identify and, if desired, separate cells based on their desired characteristics, for instance by using a Fluorescence Activated Cell Sorter (FACS). The application provides numerous methods which greatly simplify and reduce the time necessary to carry out previously-known procedures, and offers new approaches as well. The studies carried out so far involving beacons and living cells do not show a significant difference above control. The problem is eliminated first by using stronger fluorophores, and also by modifying beacons such that the number of nucleotides forming the stem portion of the stem-loop molecule are longer than the classical length of five or six nucleotides that is used. This makes it more likely for the molecule to maintain in its stem-loop, nonfluorescent state in the absence of target sequence, thereby reducing background.

It is possible with the methodology described hereinabove to generate stably transfected cell lines which express RNAs with different roles; that is, some which neither code for protein nor act as antisense RNA but which are expressed by cells nevertheless, others which serve as messenger RNAs, and others which are antisense RNAs to the two classes already listed. Such other RNAs include structural RNAs such as ribosomal RNAs, hnRNA, snRNA, etc.

1. Generating Protein-Expressing Cell Lines

Some of the most tedious steps involved in generating cell lines are eliminated by the application of molecular beacons as described herein. Following drug-selection of cells transfected with a DNA construct encoding a desired gene as well as drug resistance, one introduces into these cells molecular beacons designed to recognize the message of the gene of interest. Those cells transcribing the gene will fluoresce. Subsequent FACS analysis results in the isolation of the fluorescent cells which are then grown to give rise to cell lines expressing the gene of choice.

If the beacon designed to recognize a message of interest is able to detect endogenously existing target sequences, the proportion of these in comparison to the proportion of the target sequence produced by transfected cells is such that the sorter is able to discriminate the two cell types. Alternatively, the issue of endogenous fluorescence is eliminated by tagging the gene of interest with an epitope tag and designing the beacon so that it recognizes the nucleotide sequence encoding the tag. These nucleotides can either be in frame with the message of the gene or out of frame with it, depending on whether one wishes to tag the protein produced.

Additionally, the level of expression of the gene of interest in any given cell may vary. The FACS is applied here to evaluate expression levels; it is used to differentially select individual cells expressing the same gene.

2. Generating Antisense-Expressing Cell Lines

There are several studies describing the generation of cell lines which express not RNA that encodes a protein, but rather one that is the antisense of a gene or portion of a gene. Such methods aim to reduce the amount of a specific protein in a given cell. The steps described above for the generation of protein-expressing cell lines are equally applicable here and virtually identical except that here the beacon is designed to detect an RNA which is an antisense RNA.

Not all attempts at making stably transfected antisense-expressing cell lines result in cell lines where the expression of the targeted protein is affected sufficiently. This difficulty has made it less worthwhile to pursue the production of such cell lines. However, given the ease of the procedure described here, one easily assays the effectiveness of numerous different genetic sequences for their ability to yield active antisense expressing cell lines.

3. Differentiating Between Cells Based on Cell Surface-Localized Antigens

Immunologists and others have long used the FACS to sort cells. In accordance with the present invention, to detect the presence of cell surface localized protein, a beacon is made that has as its target the mRNA encoding the protein of interest. The beacon is introduced into cells by transfection and the cell sorter is then used to isolate positive-scoring cells.

Additionally, FACS is currently used to sort cells based on their expression of up to three cell surface-localized proteins. This feature of the FACS is carried out by use of molecular beacons as described herein if a combination of beacons is used, each targeted to the mRNA of one of the proteins of interest, and each labeled differently. Multiple rounds of sorting are performed to sort cells based on greater than three expressed RNAs.

4. Assaying Cells for the Expression of Specific RNAs and Quantifying the Level of RNA Expression in Cells If the target RNA of a molecular beacon that is introduced into a cell is present, the cell will fluoresce. This information can be qualitatively assessed by use of the Fluorescence Microscope or the FACS, and it is also quantifiable by either of these. For instance, instead of performing in situ reverse-transcription polymerase chain reaction (RT-PCR) on slices of tissues to determine a pattern of expression for a particular RNA, a beacon is used to carry out the same experiment. Moreover, using a combination of differently fluorescent beacons, each targeting a specific RNA, one assays for the presence or quantity of several RNAs of interest in one step.

5. Localization of Antigens in Combination with Detection of RNAs in Cells and Tissues Using fixed cells or tissue slices, one uses immunocytochemistry to describe the localization of the protein antigens recognized, and using Molecular Beacon targeting specific RNAs, one co-localizes in the same samples the RNAs of interest. It has been shown that Molecular Beacons targeted to RNAs function in fixed cells.

6. Generating Cell Lines Expressing Multiple Proteins

Using the methods of the present invention, one very quickly generates stably transfected cell lines expressing any number of proteins, even without the need to maintain these cells in the presence of a mixture of numerous selective drugs. Following gene transfection and drug-selection, a combination of molecular beacons, one to each protein message, is introduced into the cells. By designing the loop sequence of each beacon to hybridize to the mRNA of only one of the genes or to the nucleotide sequence of only one of the epitope tags (see above) with which the messages may be associated, each beacon is designed to recognize the mRNA encoded by only one of the genes. The cells are then sorted by FACS. By selecting for one, two, or all three fluorescent signals, a variety of cell lines is generated in a single application.

One may have a need to produce a cell line expressing more than three RNAs of interest. For instance, it would be highly informative to have a cell line in which are over-expressed all of the proteins and RNA sequences thought to be involved in the formation of a particular complex. To achieve this, the steps described above are repeated using cells already expressing a combination of RNAs as the host cells into which would be transfected additional constructs encoding additional RNAs.

If multiple RNAs to be expressed are all cloned into constructs conferring upon cells resistance to the same drug, FACS is used to isolate cells expressing all of the desired RNAs. Because the sequences are stably integrated into the genome, the cells do not lose expression of any of the sequences. However, it is possible that one or more of the sequences could be lost. If this is the case, one increases the concentration of the selective drug in the media in which these cells are grown, making this possibility less likely. Alternatively, one uses constructs each of which confers resistance to a different drug, and maintains cells in a mix of appropriate drugs. Also, a subset of the constructs to be stably transfected into cells are chosen so as to encode a resistance gene for one drug, and another subset to encode a resistance gene for another drug.

Moreover, if some cells of a cell line lose an RNA of interest, then as one resort, the first experiment as described above is performed to isolate the cell line is repeated and new cells obtained. Alternatively, the mixture of cells described are analyzed by FACS, with the aim of re-isolating cells expressing all of the desired RNAs. This is a very useful procedure as it again yields cells which give rise to a cell line with the same genetic make-up of the original cell line selected.

The approaches described above yield an unlimited supply of cells expressing any combination of proteins and RNA sequences, amenable to virtually unlimited methods of analysis. Yet it is possible that a protein that is overexpressed may be toxic to the cell, and as will be discussed later, this possibility can be readily addressed.

It should be noted that the ease with which it is possible to re-isolate cells expressing all of the desired RNAs from cell line clones where the population of cells includes some cells which no longer express all of the RNAs makes it possible to maintain cell lines in the presence of no drug or minimal concentrations of drug.

7. Generating Cell Lines Dramatically Over-Expressing One or More Proteins

For each gene that is to be highly over-expressed, for example, two or more sequences for the same gene are first cloned into DNA constructs conferring drug resistance. Each of the multiple sequences for each gene is designed to include the sequence encoding a different epitope tag. Following transfection of the DNA constructs into cells and subsequent drug-selection, molecular beacons, each of which is targeted to only one epitope tag and differentially fluorescently labeled, are introduced into the cells and the cell sorter is used to isolate cells positive for their signals. Such cells have integrated into their genomes at least one copy of each of the differentially epitope sequence tagged genes, and thus the expression of the sequence of interest occurs from an increased number of copies of essentially the same sequence of interest. This method is used in conjunction with the use of the FACS to pick out those cells scoring most intensely for the signal of each fluorophore.

8. Generating Cell Lines Expressing Multiple Antisense RNAs

Stably transfected cell lines producing multiple antisense messages are created as follows. Such antisense messages target either mRNAs or other RNAs. One selects cells which express to different levels any one of the antisense sequences transfected. Through repeated rounds of stable transfections, one readily selects cells that would give rise to stably transfected cell lines which express the antisense message of an unlimited number of RNAs.

Of course, cells expressing other RNAs other than antisense RNAs are preparable by the methods described herein. Such RNAs include but are not limited to mRNA, rRNA, other structural RNAs, hnRNA, or snRNA.

9. Generating Cell Lines Which are Functional Knock-Outs for One or More Proteins The methods of the present invention provide the means to prepare functional knock-outs in cultured cells. This eliminates the need to try to decipher the role of human proteins by studying their knock-out characteristics in yeast or mice. One generates cell lines which are functional knock-outs of any one protein of interest by generating cells expressing from multiple loci virtually the same antisense RNA to a unique RNA sequence. For instance, one stably transfects into cells multiple constructs each of which would encode the antisense RNA for a particular gene. Here each antisense RNA sequence differs only in that each would be tagged with the nucleotide sequence of a unique epitope tag. One selects those cells expressing all of the differentially-tagged antisense RNAs. Because the FACS is used to quantify fluorescence as previously described, this feature enables one to select for those cells most strongly expressing any one or more of the antisense sequences.

Importantly, different antisense sequences targeting the same gene are used in this approach. For instance, some of the antisense RNAs, the expression of which is selected for by using molecular beacons and the FACS, is designed so as to target a particular region of the messenger RNA for the gene, whereas others are designed such that they target an alternate portion of the same messenger. In order to generate cell lines which are functional knock-outs of a protein of interest, one stably transfects into cells as many genetic sequences encoding similar or different antisense RNAs to the same gene of interest as is necessary for the production of a cell line which exhibits no detectable levels of expression of the protein of interest, or alternatively, acceptably low levels of expression.

Moreover, one generates cell lines in which are functionally knocked-out multiple proteins by repeating the procedure described above while targetting any number of sequences to be knocked-out functionally by antisense. For instance, to study the function of a complex of proteins, one knock-outs all or any combination of the proteins making up the complex.

10. Generating Cell Lines Which are Functional Knock-Outs of Only Selected Alternatively Spliced Forms of One or More Genes Differentially spliced versions of a single gene are often translated into proteins with differing functions. Using the methods of the present invention, one generates cell lines which are functional knock-outs of only selected alternatively spliced forms of one or more proteins. For example, by designing antisense that would target only those alternatively spliced versions of the messenger RNA of the gene that one would like to eliminate from the cell, one functionally knock-outs all of the alternatively spliced RNAs of the gene of interest except for those alternatively spliced messages which are of interest.

11. Generating Cell Lines Expressing One or More Proteins While Functionally Knocked-Out of One or More Other Proteins It is possible with the methodology described hereinabove to generate stably transfected cell lines which express RNAs with different roles; that is, some which neither code for protein nor act as antisense RNA but which are expressed by cells nevertheless, others which serve as messenger RNAs, and others which are antisense RNAs to the two classes already listed. These include but are not limited to structural RNAs such as ribosomal RNA, hnRNA, snRNA, and other non-mRNAs.

For instance, for a given group of proteins that is thought to interact with each other, one can study their interactions by generating stably transfected cell lines in which one or more of the proteins of interest are functionally knocked-out by the cell's expression of antisense RNAs. The function of the remaining proteins of interest in the cell can then be studied, but perhaps more interestingly, such a cell could be further altered by further manipulating it such that it will now over-express one or more of the remaining proteins of interest. Such a train of thought can be pushed infinitely further, allowing one to over-express or eliminate the expression of additional proteins in cells.

The methods described above transform the science of mammalian cells and other cells amenable to maintenance in tissue culture to allow for many genetic manipulations never before possible. For the first time, it is possible to generate functional knock-outs in human cells, and to also them have these over-express proteins. Again, it is possible that over-expression of certain proteins or a functional knock out of certain proteins may be lethal to cells. This is a problem that will be addressed below.

12. Generation of Transgenic Mice

For some purposes, the study of cells in culture is not sufficient. The methodology described above, however, also lends itself towards the manipulation of embryonic stem cells. Embryonic stem cells may be obtained that could either express multiple proteins or act as functional knock-outs of multiple proteins or a subset of the alternatively spliced forms of multiple proteins, etc., following the above procedures. Such embryonic stem cells are then used as the basis for the generation of knock-out animals. Using these procedures, one determines before an attempt is made at generating a knock-out animal if the experiment will result in a lethal phenotype. For instance, if a protein that is essential is functionally knocked-out in embryonic stem cells, then such cells may not survive following their isolation by the FACS.

13. Generating Inducible Stably Transfected Cell Lines

The over-expression or the lack of expression of certain proteins or RNAs in cells may be lethal. Yet it may be of critical importance to study a cell over-expressing a toxic protein or RNA, or one which is a functional knock-out of a protein or RNA without which the cell is unable to survive. To this end, one generates stably transfected cells where selected RNAs having such deleterious effects on the cell are under the control of inducible promoters. To isolate is such cell lines, the transfected and drug-selected cells are first minimally induced to affect transcription of the inducible genes, and the cells are then be subjected to FACS analysis following the transfection into them molecular beacons designed to recognize the appropriate RNAs. The cells obtained are maintained such that the toxic RNAs are uninduced and transcribed only when necessary.

Inducible systems may be advantageous for applications other than the expression of toxic RNAs. For instance, one induces the expression of genetic sequences stably transfected into cells at a certain point during the cell cycle of a synchronized cell line. Alternatively, if the expressed products of a set of one or more stably transfected genetic sequences is thought to act on the expressed products of another set, then it is of interest to clone the genetic sequences of the first set under the control of one inducible promotor, and those of the second set under the control of a second inducible promotor. By varied inductions, one studies the expressed products encoded by either set of genetic sequences in either the absence or the presence of the expressed products of the other set.

14. Detecting Genetic Recombinational Events in Living Cells and the Subsequent Isolation of Non-Recombined or Differentially Recombined Cells Parallel to the use of molecular beacons to detect the recombinational events that lead to stable cell lines is the use of beacons to detect and isolate from a mixture of living cells those cells which have undergone other specific recombinational events. The same principle can be used to assay for VDJ recombination, translocation, and viral genome integration, for instance.

In cellular recombinational events, for instance, one sequence of genomic DNA is swapped for another. If a DNA sequence encoding a region where a recombinational event occurred is transcribed into RNA, then the presence of such an event is detected for by a molecular beacon designed to recognize either the RNA transcribed from the unrecombined DNA sequence, or that which is transcribed from the recombined sequence. Such an assay is also carried out by the Fluorescent Microscope. If one would like to separate from each other cells which have recombined from those which have not, then one subjects the cells to the FACS and sorts them. In addition, the FACS is used to sort out cells based on the presence or absence in them of numerous recombinational events.

15. Sorting Cells on the Basis of Expressed RNAs

The use of molecular beacons as described herein allows cells to be sorted based on their expression of internally localized proteins as well as proteins against which one may not be able to generate antibodies. For instance, starting from a mixed population of cells, one isolates those cells which express internally localized proteins of interest by designing molecular beacons which recognize the mRNAs which give rise to these proteins. These molecular beacons are transfected into the mixture of cells and the FACS is used to sort them as appropriate. Multiple rounds of sorting may be carried out.

Additionally, a researcher may be interested, for instance, in isolating cells which are induced upon stimulation by a cytokine to express the mRNA of one or more specific proteins from those which fail to be similarly induced. To this end, a mixture of cells is first induced by the cytokine, then transfected with beacons each of which is designed to recognize the mRNA that would give rise to one of the proteins of interest. The FACS is then used to isolate those cells which score positive for the mRNA of interest. In an alternative embodiment, one also assays cells infected with a virus, for instance, for their expression of a particular gene.

It is possible with the methodology described hereinabove to detect cells positive for the presence of RNAs with different roles; that is, some which neither code for protein nor act as antisense RNA but which are expressed by cells nevertheless, others which serve as messenger RNAs, and others which are antisense RNAs to the two classes already listed. These include but are not limited to structural RNAs such as ribosomal RNA, hnRNA, snRNA, and other non-mRNAs.

16. In Vivo detection of Nucleic Acids, in Connection with the Subsequent Selection of Cells Because the chemistry required is well characterized, one can modify molecular beacons in many ways, yielding new possibilities. For instance, cells expressing a specific mRNA the expression of which leads to malignant transformation of the cell are selectively destroyed, while cells not expressing this mRNA are more or less unaffected, as described below. A molecular beacon is selected consisting of an oligonucleotide designed to recognize and hybridize to a specific sequence of nucleic acid contained in a gene of interest that is transcribed in some of a mixture of cells. The oligonucleotide has covalently attached at one end a protease, and at its other end one or more molecules of the inhibitor of the protease, for example a peptide inhibitor. Note that it is important for the oligonucleotide used to synthesize such a beacon to have ends that can hybridize with each other, as is the case with molecular beacons. So long as the molecule described maintains its stem-loop structure, the peptide inhibitor on one end of the molecule will be sufficiently close to the protease which is on the other end so as to affect inhibition. For ease of discussion, such molecules just described will be referred to as Probe Proteases.

Upon transfection of probe proteases into cells expressing the RNA that is recognized by a Probe Protease, the Probe Protease hybridizes to its target. This causes activation of the protease as in its hybridized state, the protease is no longer in the vicinity of its peptide inhibitor. A cell in which the target of such a Probe Protease is present and recognized is damaged and is thus selected against.

Additionally, Probe Proteases are useful in various other applications. For example, given a mixture of cells in which some of the cells are infected by a particular virus, one introduces into the cells a Probe Protease that targets a specifically viral mRNA. Cells which carry such an mRNA activate the proteolytic activity of the Probe Protease they contain, and this destroys these cells.

It is possible with the methodology described hereinabove to generate stably transfected cell lines which express RNAs with different roles; that is, some which neither code for protein nor act as antisense RNA but which are expressed by cells nevertheless, others which serve as messenger RNAs, and others which are antisense RNAs to the two classes already listed.

Based on foregoing description, the following methods may be carried out.

A method for generating a cell line expressing at least one preselected protein is provided comprising the steps of:
- a) transfecting cell lines with at least one DNA construct encoding said at least one preselected protein and at least one drug resistance marker;
- b) selecting for cells resistant to a drug to which said marker confers resistance, said cells transcribing the at least one DNA construct and the at least one drug resistance marker;
- c) exposing said selected cells to a first molecular beacon that fluoresces upon hybridization to an RNA transcript of said at least one preselected protein;
- d) isolating said cells that fluoresces;
- e) generating a cell line expressing said at least one preselected protein by growing said isolated cells.

In this method, isolating said cells that fluoresce may be carried out using fluorescence activated cell sorter technology. The cell line may be further prepared to express a second preselected protein, in either a simultaneous or sequential fashion, the additional steps including transfecting the cell line with a second DNA construct encoding a second preselected protein and a drug resistance marker; selecting for cells expressing said second marker; exposing said cells to a second molecular beacon which fluoresces upon hybridization to an RNA transcript of said second preselected protein and isolating cells that exhibit fluorescence of each of said at least one and said second mRNA transcripts. Presently, current technology allows the detection of up to three different fluorophores during a sorting procedure, at the present, the above procedure may be repeated simultaneously to obtain the expression of up to three different proteins. If desired, a cell line expressing three different proteins may then be used as the starting point for the introduction of more proteins following the procedure.

The DNA construct used for transfection may encode a single gene and a drug resistance marker, or additional genes with corresponding markers. Successful transfection of each gene may be achieved by selection with the corresponding drug. As noted above, whether the introduction of additional genes is done simultaneously or sequentially, the number of expressed messages detectable at one time may be limited by the fluorescence technology, but the method can be carried out repeatedly to add more genes. If up to three fluorophores can be detected, three genes can be introduced at a time.

A related approach is disclosed in which an epitope tag associated with the transfected gene is used as the target for the molecular beacon, allowing the selection of cells expressing proteins whose mRNAs may be difficult to identify over background, for example, if the molecular beacon detects a closely related RNA species. Accordingly, a method for generating a cell line expressing at least one preselected protein is provided comprising the steps of:
- a) transfecting a cell line with at least one DNA construct encoding said at least one preselected protein, at least one drug resistance marker and at least one first epitope tag;
- b) selecting for cells resistant to a drug to which said marker confers resistance, said cells transcribing the at least one DNA construct and the at least one drug resistance marker;
- c) exposing said cells to a first molecular beacon that fluoresces upon hybridization with the RNA transcript of said first epitope tag;
- d) isolating said cells that fluoresce; and
- e) generating a cell line expressing said at least one preselected protein by growing said isolated cells.

The methods are essentially the same as that described previously, except that the molecular beacon that are used are designed to recognize the epitope tag rather than the RNA transcript of the desired introduced protein. A benefit of this procedure over the previous one is that only a small number of molecular beacons, corresponding to the number of different epitope tags, is needed to prepare a large number of different cell lines expressing one or more proteins. As the fluorescence sorter technology is now limited to three fluorophores, only three different beacons are necessary of this method. Should the technology later allow increased numbers of fluorophores to be detected simultaneously, this may be increased. However, up to three introduced proteins at one time can be added, then the cells successfully transfected with the three genes can be used as the starting point for the addition of further genes.

Examples of epitope tags which may be used in the invention, and to which beacons may be prepared include but are not limited to HA (influenza hemagglutinin protein), myc, his, protein C, VSV-G, FLAG, or FLU. These and other epitope tags are known to one of skill in the art. As used herein, the epitope tag provides a unique nucleic acid sequence for recognition by a molecular beacon. Whether or not the nucleic acid sequence is in frame or out of frame with the encoded protein in a construct is not critical; the molecular beacon can recognize either. Thus, the transcribed RNA bearing the epitope tag nucleic acid sequence does not need to be translated for detection of the transcript by the molecular beacon.

Of course, the foregoing method may be used to introduce more than one protein into the cells, further steps performed simultaneously or sequentially including transfecting the cell line with a second DNA construct encoding the second preselected protein, a second drug resistance marker and a second epitope tag, selecting for cells expressing said second marker; exposing said cells to a second molecular beacon that fluoresces upon hybridization with the RNA transcript of said second epitope tag, and isolating said cells that exhibit fluorescence of each of said first and said second epitope tag. The second epitope tag may be in frame or out of frame with the portion of the DNA sequence encoding said second protein.

The selection of successfully transfected cells is carried out by standard procedures of growing cells in the presence of the drug against which the drug resistance marker is provided. If selection is for two different markers, these can be selected simultaneously or sequentially. If the same drug resistance marker is used on two different transfected constructs, a higher level of drug may be needed to select for cells transfected with both construct, to account for dose effect.

The foregoing methods for preparing cell lines expressing one or more proteins may be just as easily applies to generating cell lines expressing one or more antisense RNA molecules. The method comprises:
- a) transfecting a cell line with a DNA construct encoding said at least one preselected antisense RNA molecule and at least one drug resistance gene;
- b) selecting for cells resistant to a drug to which said marker confers resistance, said cells transcribing the at least one DNA construct and the at least one drug resistance marker;

c) exposing said cells to a molecular beacon that fluoresces upon hybridization to said antisense RNA molecule;

d) isolating said cells that fluoresce; and e) generating a cell line expressing said preselected antisense RNA sequence by growing said isolated cells.

All details of these methods are as described above. In the instance where a beacon cannot detect the particular mRNA., the epitope tag method may be used, namely:

a) transfecting a cell line with a DNA construct encoding said at least one preselected antisense RNA molecule, at least one drug resistance marker and a first epitope tag nucleotide sequence;

b) selecting for cells resistant to a drug to which said marker confers resistance, said cells transcribing the at least one DNA construct and the at least one drug resistance marker;

c) exposing said selected cells to a first molecular beacon that fluoresces upon hybridization to a mRNA transcript of said first epitope tag;

d) isolating said cells that fluoresce; and e) generating a cell line expressing said at least one preselected antisense RNA molecule by growing said isolated cells.

As noted above, the advantage to the epitope tag detection method is that separate beacons to each antisense RNA do not have to be made; beacons are needed to only a few epitope tags, which can be used in successive steps to introduce a large number of antisense molecules, or over expression of one molecule into a cell line. Naturally, the foregoing methods may be repeated simultaneously or successively to introduce two or more antisense RNA molecules in a given cell line.

In addition, cells made to express a particular protein or proteins may be used as the starting point for creating cells expressing proteins and antisense RNA molecules. Of course, the cells expressing the antisense molecules may be used as the starting point for adding expressed proteins, using the methods herein. Simultaneous transfection of proteins and antisense molecules, with corresponding beacons and, if desired, epitope tags, may also be performed., The various combinations of the aforementioned procedures is embraced herein.

Likewise, methods are provided for isolating cells expressing at least one protein comprising the steps of:

a) providing cells suspected of expressing said at least one protein;

b) exposing said cells to at least one molecular beacon that fluoresces upon hybridization with a mRNA transcript encoding said at least one protein;

c) isolating said cells that fluoresce.

These methods are particularly useful for protein that are cell surface-localized protein or an intracellular protein. They do not require the use of probes for the proteins themselves, which may be more difficult or will affect the cell such that further experiments cannot be performed. More than one protein can be identified using a plurality of molecular beacons, up to the number simultaneously detectable by the technology used for isolation.

Naturally, the aforementioned procedures may be used to quantify the level of at least one RNA transcript expression in a biological sample comprising the steps of:

a) exposing the biological sample to a first molecular beacon which fluoresces upon hybridization with said RNA transcript;

b) quantitating the level of fluorescence in the biological sample; and c) correlating the level of fluorescence with said level of the at least one mRNA transcript.

The biological sample may be a cellular sample or a tissue sample; these may be fixed, for example, with formaldehyde, glutaraldehyde, or any number of known cellular fixatives which do not interfere with the detection of RNA using molecular beacons.

The detected RNA transcript may be RNA that encodes a protein, a structural RNA, and an antisense RNA. The fluorescence may be quantitated by fluorescence microscopy or fluorescence-activated cell sorter technology. Additional RNA species may be quantitated simultaneously using a second molecular beacon which fluoresces upon hybridization to a second RNA transcript.

In another use of the foregoing methods, a method is provided for generating a cell line which overexpresses at least one protein. This is achieved by transfecting cells with two or more sequences encoding the same protein, selecting for and identifying expression through epitope tags associated with the separate copies of the transcript. The steps include:

a) transfecting cells with at least-two DNA sequences, said sequences each having a portion encoding the protein, at least one epitope tag, and at least one drug resistance marker; and a portion encoding the same protein, at least one second epitope tag, and at least one second drug resistance marker;

b) selecting for cells transfected with the at least two DNA sequences by expression of the first and the second drug resistance markers;

c) exposing the selected cells to a first and a second molecular beacon, each which fluoresces upon hybridization to the nucleotide sequences of RNA transcripts of said first and second epitope tags respectively;

d) isolating cells that exhibit fluorescence of each of said first and second molecular beacons; and e) generating a cell line overexpressing said at least one preselected protein by growing the isolated cells.

As noted above, if the same drug resistance marker is used for each copy of the gene, a higher level of drug may be needed to select for cells transfected with both sequences. As in the previous methods, the at least two DNA sequences may reside on the same construct. The first and said second epitope tags may each independently be in frame or out of frame with the protein.

The aforementioned procedure is easily applicable to generating cells overexpressing at least one antisense RNA molecule. The method comprises the steps of:

a) transfecting cells with at least two DNA sequences, the sequences each having a portion encoding said antisense RNA molecule, at least one epitope tag, and at least one drug resistance marker; and a portion encoding said antisense RNA molecule, at least one second epitope tag, and at least one second drug resistance marker;

b) selecting for cells transfected with said at least two DNA sequences by expression of said first and said second drug resistance markers;

c) exposing said selected cells to a first and a second molecular beacon, each which fluoresces upon hybridization to the nucleotide sequences of RNA transcripts of said first and said second epitope tags respectively;

d) isolating said cells that exhibit fluorescence of each of said first and second molecular beacons; and e) generating a cell line overexpressing said at least one preselected antisense RNA molecule by growing said isolated cells.

The details are the same as those described above.

Introduction of antisense RNA molecules in cells is useful for functionally eliminating one or more proteins from the cell. Following the above methods, a method is provided for generating cells functionally null for expression of at least one preselected protein comprising the steps of providing in said cells a plurality of antisense RNAs to said preselected protein, each provided in accordance with the aforementioned methods, wherein said plurality of antisense RNA to said at least one preselected protein binds essentially all mRNA transcripts of said at least one preselected protein. The preselected protein may be an alternatively spliced form of a gene product. Following similar lines, a method is provided for generating a transgenic animal that is a functionally null-expressing mutant of at least one preselected protein comprising carrying out the steps described hereinabove utilizing embryonic stem cells, determining the viability of said stem cells functionally null expressing said preselected protein, and using said viable embryonic stem cells to produce said transgenic animal.

Likewise, a method is provided for generating a cell line which is functionally null expressing at least one protein and overexpresses at least one other protein comprising carrying out the methods herein on the same cells. In similar fashion, a method is provided for generating a cell line expressing a lethal antisense RNA under control of an inducible promoter by carrying out the method herein wherein the transfection step is performed in the presence of a minimal amount of an inducer.

A method is provided herein for identifying genetic recombinational events in living cells comprising the steps of:

a) exposing a cell to a molecular beacon that fluoresces upon hybridization with a RNA sequence selected from the group consisting of that transcribed from a recombined sequence and that transcribed from the nonrecombined sequence; and b) detecting said cells expressing said RNA sequence.

The present invention is also directed to a novel form of molecular beacon which, in contrast to the fluorescent properties exhibited by prior art molecular beacons on binding to their target nucleic acids, exhibit proteolytic activity upon such binding. Such its proteolytic activity may be used for detection purposes, but also to degrade particular protein sequences in a cell should the mRNA encoding the protein be present in the cell. For example, a protease which specifically cleaves a viral protein maybe activated should transcription of the virus become activated, such as in a latent infection.

Preferably, the proteolytic enzyme inhibitor is a peptide, although other molecules including metals and metal chelators are also useful, to provide reversible inhibition of the enzyme upon interaction with the inhibitor. Examples of useful pairs of proteolytic enzymes and inhibitors of the proteolytic enzyme include but are not limited to aminopeptidase and amastatin, trypsin-like cysteine proteases and antipain, aminopeptidase and bestatin, chymotrypsin like cysteine proteases and chymostatin, aminopeptidase and diprotin A or B, carboxypeptidase A and EDTA, elastase-like serine proteases and elastinal, and thermolysin or aminopeptidase M and 1,10-phenanthroline.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

General Protocol

Starting Material

Molecular Beacons may be introduced into cells which are not expressing any RNAs from plasmids, or they may be used to detect RNA messages encoded from plasmids. The method of introduction of the beacons into either of these two types of cells is identical. The protocol below only requires that the cells to be analyzed are separable from each other and are amenable to FACS analysis.

1) As described more thoroughly in the description of the invention, beacons can be used in conjunction with FACS to sort out cells of a tissue based on expression or lack of expression within cells of specific RNAs. To this end, cells must first be separated from each other by standard and well established methods such as homogenization and further chemical treatment. Appropriate beacons may then be introduced into such cells according to the protocol below.

2) Second, one may use beacons to select for cells expressing particular RNAs encoded by plasmids that have been transfected into a population of cells. To this end, one must first transfect into a culture of cells a plasmid or plasmids encoding the desired RNAs. Beacons may then be generated to recognize these RNAs, as described in more detail in the description of the invention. Transfection of the plasmids into cells can be accomplished through a vast variety of methods using either ones own reagents or kits obtained from biotechnical firms (Qiagen, Promega, Geneporter, Invitrogen, Stratagene, etc.), following the manufacturers' instructions. The plasmids should be chosen such that each confers resistance to an antibiotic. Following the of these plasmids into cells and a brief period for the recovery of the cells (usually 24 hours), the cells would be subjected to the appropriate antibiotics such that only those cells to which the plasmids have conferred antibiotic resistance will survive. This generally takes three to four days, depending both on the cell type and the antibiotic used.

The result is that a pool of cells remain and all of these would be resistant to antibiotics, but only a small fraction of which express the RNAs of interest. To select for the cells expressing the desired RNAs, the protocol below may be followed.

EXAMPLE 2

Selection of Cells Using Beacons

1) Transfect beacons into cells: Beacons must be designed such that they will recognize the desired RNA either by hybridizing to a sequence endogenous in the RNA or by hybridizing to a tag that is added to the native RNA sequence. The design of beacons is elaborated upon in the description of the invention.

Transfection may be carried out by a vast variety of methods, similar to the transfection of plasmids into cells. The method employed should be chosen based on the cell type being used as some cells respond better to some transfection methods over other methods. Transfection should be performed according to the instructions of the manufacturer of the transfection reagent used.

Transfection of beacons into cells may be carried out either on cells in suspension or on cells growing on solid surfaces, depending on the transfection reagent used.

2) Following the transfection of beacons into cells, the cells may then be subjected to FACS analysis. FACS can be used to sort out cells positive for any one or more of the beacons used. It can also be used to sort out cells based on the intensity of the beacons' signal, thereby allowing the researcher to select cells which express RNAs to different degrees.

EXAMPLE 3

Generation of Cell Lines Expressing One or More RNAs

Following FACS selection, the positive-scoring cells can be maintained in appropriate medium as described in more detail in the description of the invention. This cells would give rise to cell lines expressing the RNAs of interest.

Concentration of the Beacon

The concentration of beacon to be used depends on several factors. For instance, one must consider the abundance within cells of the RNA to be detected and the accessibility of this RNA to the beacon. For instance, if the RNA to be detected is present in very low amounts or if it is found in a portion of the RNA which is not readily accessible based on the three-dimensional folding of the RNA, then more beacon should be used here then in cases where the RNA to be detected is in high abundance and where the site recognized by the beacon is fully accessible. The exact amount of beacon to be used will have to be determined empirically for each application.

This can be accomplished by introducing different amounts of beacons into different groups of cells and selecting the condition where background fluorescence is low and where signal is high (the condition where not all but some of the cells score positive for the beacon).

What is claimed is:

1. A method for generating a cell nine expressing at least one RNA of interest, comprising the steps of:
    a) introducing into cells DNA encoding said at least one RNA of interest;
    b) exposing said cells to at least one molecular beacon that fluoresces upon hybridization to said at least one RNA of interest, wherein said molecular beacon comprises nucleotides complementary to the RNA of interest and nucleotides mutually complementary;
    c) isolating said cells that fluoresce; and
    d) generating a cell line expressing said at least one RNA of interest by growing said isolated cells.

2. A method for generating a cell line that expresses two or more RNA molecules of interest, comprising the steps of:
    a) introducing into cells DNA encoding a first RNA of interest;
    b) introducing into said cells DNA encoding at least one additional RNA of interest;
    c) exposing said cells to at least one molecular beacon that fluoresces upon hybridization to said first RNA of interest, wherein said molecular beacon comprises nucleotides complementary to the first RNA of interest and nucleotides mutally complementary;
    d) exposing said cells to at least one molecular beacon that, fluoresces upon hybridization to said at least one additional RNA of interest, wherein said molecular beacon comprises nucleotides complementary to the additional RNA of interest and nucleotides mutually complementary;
    e) isolating cells that exhibit fluorescence upon hybridization of said molecular beacons to their respective RNA of interest; and
    f) generating a cell line expressing said two or more RNA molecules of interest by growing said isolated cells.

3. The method of claim 1 or 2, wherein the step of isolating said cells that fluoresce is carried out using fluorescence activated cell sorter technology.

4. The method of claim 2, wherein said steps of said first RNA of interest are performed either simultaneously or sequentially with the corresponding steps of said at least one additional RNA of interest.

5. The method of claim 1 or 2, wherein the RNA of interest comprises one or more of a messenger RNA that encodes a protein, an antisense RNA molecule, a structural RNA, a ribosomal RNA, an hnRNA and an snRNA.

6. A method for generating a cell line expressing an RNA of interest, comprising the steps of:
    a) introducing into cells DNA encoding said at least one RNA of interest and at least one epitope tag;
    b) exposing said cells to at least one molecular beacon that fluoresces upon hybridization with the RNA transcript of an epitope tag, wherein said molecular beacon comprises nucleotides complementary to the RNA transcript of the epitope tag and nucleotides mutually complementary;
    c) isolating said cells that fluoresce; and
    d) generating a cell line expressing said RNA of interest by growing said isolated cells.

7. A method for generating a cell line expressing two or more RNA molecules of interest, comprising the steps of:
    a) introducing into cells a first DNA encoding a first RNA of interest and at least one epitope tag;
    b) introducing into said cells DNA encoding at least one additional RNA of interest and at least one epitope tag;
    c) exposing said cells to at least one molecular beacon that fluoresces upon hybridization with the RNA transcript of an epitope tag for said first RNA of interest, wherein said molecular beacon comprises nucleotides complementary to the RNA transcript of the epitope tag and nucleotides mutually complementary;
    d) exposing said cells to at least one molecular beacon that fluoresces upon hybridization with the RNA transcript of an epitope tag for said at least one additional RNA of interest, wherein said molecular beacon comprises nucleotides complementary to the RNA transcript of said epitope tag and nucleotides mutually complementary;
    e) isolating cells that exhibit fluorescence upon hybridization of said molecular beacons with their respective RNA transcripts; and
    f) generating a cell line expressing said two or more RNA molecules of interest by growing said isolated cells.

8. A method for generating a cell line expressing two or more RNA molecules of interest, comprising the steps of:
    a) introducing into cells DNA encoding two or more RNA molecules of interest, wherein the DNA encoding at least one of said RNA molecules of interest further encodes at least one epitope tag;
    b) exposing said cells to at least one molecular beacon that fluoresces upon hybridization with an RNA of interest, wherein said molecular beacon comprises nucleotides complementary to the RNA of interest and nucleotides mutually complementary, and at least one molecular beacon that fluoresces upon hybridization with the RNA transcript of an epitope tag, wherein said molecular beacon comprises nucleotides complementary to the RNA transcript of an epitope tag and nucleotides mutually complementary;

c) isolating said cells that fluoresce; and d) generating a cell line expressing said two or more RNA molecules of interest by growing said isolated cells.

9. The method of any one of claims 6 to 8, wherein the step of isolating said cells that fluoresce is carried out using fluorescence activated cell sorter technology.

10. The method of claim 7, wherein said steps of said first RNA of interest are performed either simultaneously or sequentially with the corresponding steps of said at least one additional RNA of interest.

11. The method of claim 8, wherein the steps relating to each of said two or more RNA molecules of interest are performed simultaneously or sequentially.

12. The method of any one of claims 6 to 8, wherein the RNA of interest comprises one or more of a messenger RNA that encodes a protein, an antisense RNA molecule, a structural RNA, a ribosomal RNA, an hnRNA and an snRNA.

13. The method of any one of claims 6 to 8, wherein the DNA encoding said epitope tag is in frame with the DNA encoding said RNA of interest.

14. The method of any one of claims 6 to 8, wherein the DNA encoding said epitope tag is out of frame with the DNA encoding said RNA of interest.

15. The method of any one of claims 2, 7 and 8, wherein said DNA encoding two or more RNA molecules of interest is on the same construct or on different constructs.

16. A method for generating a cell line that overexpresses an RNA of interest comprising the steps of:

a) introducing into cells a first DNA encoding said RNA of interest and a first epitope tag; and at least one additional DNA encoding said RNA of interest and a second epitope tag, wherein the first and second epitope tags are different;

b) exposing said cells to at least one molecular beacon that fluoresces upon hybridization with said RNA transcript of said first epitope tag, wherein said molecular beacon comprises nucleotides complementary to the RNA transcript of said first epitope tag and nucleotides mutually complementary, and to at least one molecular beacon that fluoresces upon hybridization with the RNA transcript of said second epitope tag, wherein said molecular beacon comprises nucleotides complementary to the RNA transcript of said second epitope tag and nucleotides mutually complementary;

c) isolating cells that exhibit fluorescence of at least one of said molecular beacons; and d) generating a cell line overexpressing said RNA of interest by growing said isolated cells.

17. The method of claim 16, wherein the step of isolating said cells that fluoresce is carried out using fluorescence-activated cell sorter technology.

18. The method of claim 16, wherein the steps relating to the first DNA and said additional DNA are performed simultaneously or sequentially.

19. The method of claim 16, wherein said first DNA and said additional DNA are on the same construct or different constructs.

20. The method of claim 16, wherein said RNA of interest comprises one or more of a messenger RNA that encodes a protein, an antisense RNA molecule, a structural RNA, a ribosomal RNA, an hnRNA and an snRNA.

21. The method of claim 16, wherein said DNA encoding said first epitope tag and said DNA encoding said second epitope tag are each independently in frame or out of frame with said DNA encoding said RNA of interest.

22. The method of any one of claims 1, 2, 6, 7, 8 and 16, further comprising the step of selecting the cells after step a) but prior to exposing said cells to said molecular beacons.

23. The method of any one of claims 1, 2, 6, 7, 8 and 16, wherein at least one DNA further encodes at least one drug resistance marker, and said method further comprises the step of selecting cells resistant to at least one drug to which said marker confers resistance.

24. The method of any one of claims 1, 2, 6, 7, 8 and 16, wherein said DNA is operably linked to a conditional promotor.

25. The method of claim 24, wherein said DNA encodes one or more of a messenger RNA that encodes a protein, an antisense RNA molecule, a structural RNA, a ribosomal RNA, an hnRNA and an snRNA.

26. The method of claim 24, wherein the RNA of interest is lethal to the cell.

27. The method of claim 24, wherein the promotor is inducible, and an inducer is applied prior to exposing said cells to the molecular beacon.

28. A method for isolating cells expressing at least one RNA of interest comprising the steps of:

a) providing cells potentially expressing said at least one RNA of interest;

b) exposing said cells to at least one molecular beacon that fluoresces upon hybridization with said at least one RNA of interest, wherein said molecular beacon comprises nucleotides complementary to the RNA of interest and nucleotides mutually complementary;

c) isolating said cells that fluoresce.

29. The method of claim 28, wherein said cells further potentially express one or more additional RNA molecules of interest, further comprising the steps of:

d) exposing said cells to at least one molecular beacon that fluoresces upon hybridization with said at least one additional RNA of interest, wherein said molecular beacon comprises nucleotides complementary to the additional RNA of interest and nucleotides mutually complementary; and e) isolating cells exhibiting fluorescence upon hybridization of said molecular beacon with said additional RNA of interest.

30. The method of claim 28 or 29, wherein the step of isolating said cells that fluoresce is carried out using fluorescence-activated cell sorter technology.

31. The method of claim 29, wherein said steps are performed either simultaneously or sequentially with the corresponding steps in claim 28.

32. The method of claim 28 or 29, wherein the RNA of interest comprises one or more of a messenger RNA that encodes a protein, an antisense RNA molecule, a structural RNA, a ribosomal RNA, an hnRNA and an snRNA.

33. The method of claim 32, wherein said protein is selected from the group consisting of a cell surface-localized protein and an intracellular protein.

* * * * *

UNITED STATES PATENT AND TRADEMARK OFFICE
CERTIFICATE OF CORRECTION

PATENT NO. : 6,692,965 B1
DATED : February 17, 2004
INVENTOR(S) : Shekdar et al.

It is certified that error appears in the above-identified patent and that said Letters Patent is hereby corrected as shown below:

Column 1,
Line 32, change "living-cells" to -- living cells --;

Column 3,
Line 7, change "to a the" to -- to the --;

Column 4,
Line 23, change "may be cellular" to -- may be a cellular --;

Column 5,
Line 39, change "herein before" to -- hereinbefore --;

Column 10,
Lines 58-59, change "and to also them have these over-express proteins." to -- and to also have them over-express proteins. --

Column 11,
Line 19, change "To isolate is such" to -- To isolate such --;
Line 22, change "are then be subjected" to -- are then subjected --;
Line 23, change "into them" to -- with --;

Column 14,
Line 17, change "necessary of" to -- necessary for --;
Line 60, change "applies" to -- applied --;

Column 15,
Line 11, change "mRNA.," to -- mRNA, --;
Line 42, delete "," at end of line;

Column 16,
Line 24, change "least-two" to -- least two --;
Line 34, change "each which" to -- each of which --;

Column 17,
Line 50, change "maybe" to -- may be --;

UNITED STATES PATENT AND TRADEMARK OFFICE
CERTIFICATE OF CORRECTION

PATENT NO.    : 6,692,965 B1
DATED         : February 17, 2004
INVENTOR(S)   : Shekdar et al.

It is certified that error appears in the above-identified patent and that said Letters Patent is hereby corrected as shown below:

Column 19,
Line 13, change "This cells" to -- These cells --;
Line 35, change "nine" to -- line --;
Line 57, change "mutually" to -- mutually --;
Line 60, change "that, fluoresces" to -- that fluoresces --.

Signed and Sealed this

Fourth Day of January, 2005

JON W. DUDAS
*Director of the United States Patent and Trademark Office*